United States Patent [19]

Rabo et al.

[11] Patent Number: 4,740,648

[45] Date of Patent: Apr. 26, 1988

[54] CONVERSION OF OLEFINS TO LIQUID MOTOR FUELS

[75] Inventors: Jule A. Rabo, Armonk; Peter K. Coughlin, Yorktown Heights, both of N.Y.

[73] Assignee: Union Carbide Corporation, Danbury, Conn.

[21] Appl. No.: 906,895

[22] Filed: Sep. 15, 1986

Related U.S. Application Data

[62] Division of Ser. No. 710,117, Mar. 11, 1985, abandoned.

[51] Int. Cl.$^4$ .......................... C07C 12/02; C07C 2/02
[52] U.S. Cl. ...................................... 585/415; 585/533
[58] Field of Search ................................ 585/415, 533

[56] References Cited

U.S. PATENT DOCUMENTS

| | | | |
|---|---|---|---|
| 3,236,762 | 2/1966 | Rabo et al. | 585/533 |
| 3,591,488 | 7/1971 | Eberly et al. | 502/73 |
| 3,756,942 | 9/1973 | Cattanach | 208/137 |
| 3,775,501 | 11/1973 | Kaeding | 260/673 |
| 3,827,968 | 8/1974 | Givens et al. | 208/49 |
| 4,021,502 | 5/1977 | Plank et al. | 260/683 |
| 4,150,062 | 4/1979 | Garwood et al. | 260/673 |
| 4,227,992 | 10/1980 | Garwood et al. | 208/46 |
| 4,430,516 | 2/1984 | La Pierre et al. | 585/533 |

FOREIGN PATENT DOCUMENTS 874373 2/1979 Belgium .

*Primary Examiner*—Curtis R. Davis
*Attorney, Agent, or Firm*—Gerald L. Coon

[57] ABSTRACT

Linear and/or branched claim $C_2$ to $C_{12}$ olefins are converted to hydrocarbon mixtures suitable for use as liquid motor fuels by contact with a catalyst capable of ensuring the production of desirable products with only a relatively minor amount of heavy products boiling beyond the diesel oil range. The catalyst having desirable stability during continuous production operations, comprises a steam stabilized zeolite Y catalyst of hydrophobic character, desirably in aluminum-extracted form. The olefins such as propylene, may be diluted with inerts, such as paraffins or with water, the latter serving to moderate the acidity of the catalyst, or to further moderate the activity of the aluminum-extracted catalyst, so as to increase the effective life of the catalyst.

23 Claims, No Drawings

4,740,648

CONVERSION OF OLEFINS TO LIQUID MOTOR FUELS

STATEMENT

The Government of the United States of America has rights to this invention pursuant to Contract No. DE-AC22-81PC40077 awarded by the U.S. Department of Energy.

This application is a division of prior U.S. application Ser. No. 710,117, filed Mar. 11, 1985, and now abandoned.

BACKGROUND OF THE INVENTION

1. Field of the Invention

The invention relates to the conversion of olefins to liquid motor fuels. More particularly, it relates to the conversion of such olefins to hydrocarbons boiling in the gasoline and jet fuel+diesel oil boiling range.

2. Description of the Prior Art

It is well known in the art that small olefins can be converted to gasoline range hydrocarbons. For this purpose, a molecular sieve catalyst material, such as an acidic crystalline aluminosilicate, for example ZSM-5, has been employed. When it is desired to convert such small olefins specifically to hydrocarbons boiling in the jet fuel+diesel oil boiling range, however, such an approach has not been found suitable since the use of ZSM-5 is found to experience an effective limitation at the $C_{10}$ carbon number without recycle. The use of ZSM-5 for methanol and syngas conversion was likewise found to experience this limitation. Those skilled in the art will appreciate that the end point of gasoline is about 420° F., while the diesel oil end point is about 700° F. Said 420°–700° F. hydrocarbon material comprises molecules with more carbon atoms than $C_{10}$ hydrocarbons up to about $C_{22}$ material. Hydrocarbon material in the $C_{22}$–$C_{28}$ range generally comprises heavy distillate material, with material above $C_{28}$ generally comprising wax.

While the conversion of small olefins using ZSM-5 catalyst was thus initially limited to production of gasoline range material, it has subsequently been found that, by recycling the gasoline range product back over the catalyst along with fresh feed, the product obtained can be extended into the diesel oil range. While such extension of the product range is desirable, the need for employing a recycle feature, and the costs associated with such recycle, serve to render this approach not entirely satisfactory from an overall technical-economic viewpoint. Accordingly, it is desired in the art that a more direct process be found for converting small olefins to liquid hydrocarbon fuels boiling in the jet fuel and diesel oil range, i.e. fuels containing hydrocarbons comprising $C_{10}$ up to $C_{22}$ material.

It is an object of the invention, therefore, to provide an improved process for the conversion of olefins to liquid hydrocarbon motor fuels.

It is another object of the invention to provide a catalyst capable of enhancing the conversion of olefins to such liquid fuels.

It is further object of the invention to provide an improved process and catalyst composition for producing liquid motor fuels boiling in the gasoline and jet fuel+diesel oil boiling range.

With these and other objects in mind, the invention is hereinafter described in detail, the novel features thereof being particularly pointed out in the appended claims.

SUMMARY OF THE INVENTION

Olefins are converted to liquid motor fuels in the practice of the invention by contact with a steam-stabilized, hydrophobic zeolite Y catalyst. The catalyst is advantageously in aluminum-extracted form for enhanced stability. The olefins will commonly be accompanied by a diluent, with co-fed water used as such a diluent serving to increase catalyst life in practical commercial operations.

DETAILED DESCRIPTION OF THE INVENTION

The objects of the invention are accompanied by employing a particular hydropholic zeolite Y catalyst, and modifications thereof, in the conversion of various small olefins to liquid hydrocarbons. Contrary to the results obtainable using ZSM-5 and other such zeolitic molecular sieves, the use of the zeolitic molecular sieve catalyst of the invention results in the advantageous, direct production of liquid motor fuels boiling in the gasoline and jet fuel plus diesel oil boiling range. As the catalyst of the invention is found to have desirable stability over the course of continuous processing operations, the catalyst composition and process for its use, as herein described and claimed, represent a highly desirable and practical approach to the production of liquid motor fuels boiling in the gasoline, jet fuel and diesel oil boiling range.

The feedstocks useful in the process of the invention comprise linear and/or branched chain $C_2$ to $C_{12}$ olefins, or a feedstock capable of forming such olefins in situ. $C_3$ to $C_4$ olefins are preferred feedstocks, with propylene being particularly desirable although ethylene, butenes and mixtures of such materials may also be desirably employed. The feedstock may be obtained from any convenient source, such as the total gas streams from an FCC, TCC or Riser cracking unit; a $C_3$ gas fraction from the same or different sources; a $C_4$ mixture from an unsaturated gas plant; the product of a synthesis gas or light alcohol conversion process where such are converted to olefin containing products; gas streams form a coking unit; and/or a partial product recycle in the process of the invention.

It should be noted that the olefin feedstock referred to above will commonly be employed with, or have present in any event, a diluent such as, but not limited to, $C_1$–$C_4$ paraffins (methane, ethane, propane, n-butane); inert gases, such as nitrogen, carbon dioxide; water (and/or steam); and hydrogen. Co-fed water is a particularly desirable diluent as it tends to aid in the resistance of the catalyst to coking and aging. Thus, the water diluent serves to moderate the acidity of the catalyst, or to further moderate the acidity of the aluminum-extracted catalyst variation described below, so as to increase the effective life of the catalyst. The amount of diluent present is not a critical feature of the invention, and it may generally vary from within the range of 0 to about 99 weight %, preferably between about 1% and about 95 weight %, based on the total amount of feedstock, i.e. said $C_2$–$C_{12}$ olefins and said diluent. The amount of diluent present is more preferably within the range of from 10% to about 70 weight %.

The steam-stabilized zeolite Y catalysts of hydrophobic character employed in the practice of the invention have been referred to in the art as ultrahydrophobic type Y zeolites, or simply as UHP-Y zeolites. The Y zeolites used in the invention are prepared by extensive steaming of the low-sodium forms of zeolite Y substantially as described in Belgian Pat. No. 874,373, issued Feb. 22, 1979. Such zeolites are organophilic zeolitic aluminosilicate compositions having a $SiO_2$-$Al_2O_3$ molar ratio equal to or greater than 4.5, and an essential X-ray powder diffraction pattern of zeolite Y. Furthermore, the zeolites have a crystallographic unit cell dimension, $a_o$, of less than 24.45 Angstroms, a sorptive capacity for water vapor at 25° C. and a $p/p_o$ value of 0.10 of less than 10.0 weight percent. In preferred compositions, said unit cell dimension of the catalyst is from 24.20 to 24.35 Angstroms. In addition, the water absorption capacity at 25° C. and a $p/p_o$ value of 0.10 is desirably less than 4.0 weight percent. More particularly, the $SiO_2$-$Al_2O_3$ molar ratio for certain embodiments is from 4.5 to 20.0. In a desirable embodiment in which the UHP-Y zeolite is acid extracted as discussed below, the $SiO_2$-$Al_3O_3$ molar ratio may be extended up to about 100 or more, as the alumina content of the zeolite is generally reduced to less than about 3 weight % or even about 1 weight % or less in practical commercial applications.

For the determination of the sorptive capacity of the hydrophobic zeolite Y compositions for any particular adsorbate, e.g. water, the test for zeolite sample is activated by preheating at 425° C. for 16 hours at a pressure of 5 micrometers of mercury in a conventional McBain apparatus. The temperature of the sample is thereafter adjusted to the desired value and contacted with the vapor of the test adsorbate at the desired pressure.

The hydrophobic zeolites suitable for purposes of the invention, as described above, have also been found especially suited for use as adsorbents in applications where it is desired to preferentially adsorb organic constituents from solutions or mixtures thereof with water. In the formation of synthesis gas by the distillation of coal for example, it is desirable, for environmental and economic reasons, to recover the relatively small portion of phenol present in the condensate fraction of principally water that is produced therein. For this purpose, the condensate can be contacted at ambient temperature with said hydrophobic zeolite that will selectively adsorb the phenol from said condensate. Such zeolites have also been found highly suitable for use as base materials for catalyst compositions having important commercial applications, e.g. in midbarrel hydrocracking catalyst compositions. The UHP-Y zeolites described in particular detail in the Belgian patent referred to above have been found active for the conversion of methanol to hydrocarbons ranging from methane to those boiling in the jet fuel and diesel oil boiling range up to about $C_{22}$ material.

In the practice of the invention, the olefin conversion reaction can be carried out at any suitable operating conditions, with the reaction temperature being generally from about 100° C. to about 450° C., preferably from about 240° C. to about 420° C. The catalytic conversion reaction is carried at any desired pressure level, for example at pressures of from about 0 to about 1,000 psig, typically at from about 0 to about 350 psig.

In an advantageous embodiment of the invention, the UHP-Y zeolite is acid washed or extracted essentially by the process as described in the Eberly patent U.S. Pat. No. 3,591,488, to remove a large portion of the alumina from its pores prior to its use as a catalyst for such olefin conversion. In an illustrative example, UHP-Y molecular sieve zeolite was refluxed in a 13% slurry thereof in 3.75M hydrochloric acid for three hours. The slurry was then cooled, and the supernatent was decanted therefrom. The remaining slurry was diluted in half, filtered and washed chloride-free with 0.001M nitric acid. The slurry was then washed with distilled water, dried at 110° C. for 16 hours and then at 250° C. for 16 hours and at 500° C. for an additional two hours and bottled at 400° C. The thus-treated material comprises acid-extracted, substantially alumina-free UHP-Y zeolite, otherwise referred to herein as aluminum-extracted UHP-Y zeolite.

The invention is hereinafter described with reference to certain specific examples that are presented to illustrate various embodiments of the invention. It should be understood that such examples are presented for illustrative purposes only and should not be construed as limiting the scope of the invention as set forth on the appended claims.

EXAMPLE I

In this example, the catalytic activity of the UHP-Y molecular sieve zeolite for small olefin conversion was demonstrated using a propylene-hydrogen feedstock together with co-fed steam. The UHP-Y catalyst was employed in non-aluminum-extracted form. The hydrogen will be understood to constitute a diluent, useful in the maintaining of the desired operating pressure level for the reaction. Two set of runs were carried out, one essentially at a reaction temperature of 408° C., the results of which are tabulated in Table I, the other essentially at two temperature levels, i.e., 280° C. and 340° C., the results of which are tabulated in Table II. The pressure level in the first run commenced at 172 psig and runs increased to 179 psig, while the second run was carried out at a reaction pressure that varied between 154 psig and 160 psig. The mole ratio of the components of the feedstock were 1:1:2 of hydrogen:propylene:co-fed water in the first run, and 1:1:3 in the second run. The propylene was fed to the reactor during each run at a rate of about 0.4 WHSV, i.e., weight hourly space velocity, or weight of gas/weight of catalyst/hr. Product samples of effluent gas and liquids were collected periodically. The liquid product generally had two layers, i.e., an aqueous layer and an organic oily layer, the latter sometimes having contained solids or crystals associated therewith. The effluent gases were analyzed by gas chromatography for light hydrocarbons and fixed gases, e.g., hydrogen, CO, argon, $CO_2$ and the like.

The results for such runs are shown in Tables I and II below in terms of olefin conversion, hydrocarbon selectivity of the desirable $C_5$ range material and supplemental product characterizations.

TABLE I

| Propylene Conversion (with hydrogen diluent and co-fed water) - Run 1 | | | | | |
|---|---|---|---|---|---|
| Sample No. | 1 | 2 | 3 | 4 | 5 |
| Hours on Stream | 4.17 | 7.67 | 25.17 | 31.92 | 48.58 |
| Temperature, °C. | 408 | 408 | 408 | 409 | 408 |
| $C_3H_6$ Feed, WHSV | 0.4 | 0.4 | 0.4 | 0.4 | 0.4 |
| $C_3H_6$ Conversion, % | 50.37 | 31.06 | 9.47 | 7.86 | 5.16 |
| Product Selectivity, wt. % | | | | | |
| $C_1$-$C_4$ | 77.8530 | 55.4312 | 71.0495 | 74.5822 | 78.9552 |
| $C_5$-420° F. | 22.1470 | 33.9277 | 23.8295 | 23.5314 | 20.5392 |
| 420° F.-700° F. | 0.0000 | 9.6979 | 4.3266 | 1.7192 | 0.4608 |
| $C_5$-end point | 22.1470 | 44.5688 | 28.9505 | 25.4178 | 21.0448 |

TABLE I-continued

Propylene Conversion (with hydrogen diluent and co-fed water) - Run 1

| Sample No. | 1 | 2 | 3 | 4 | 5 |
|---|---|---|---|---|---|
| Iso/normal mole ratio | | | | | |
| $C_4$ | 2.0584 | 1.1355 | 0.3955 | 0.1466 | 0.0833 |
| $C_5$ | 2.9107 | 1.0894 | 0.4038 | 0.4839 | 0.2442 |
| $C_6$ | 3.7536 | 2.0800 | 1.7256 | 1.8657 | 1.4759 |

TABLE II

Propylene Conversion (with hydrogen diluent and co-fed water) - Run 2

| Sample No. | 1 | 2 | 3 | 4 | 5 | 6 |
|---|---|---|---|---|---|---|
| Hours on Stream | 7.8 | 23.8 | 28.1 | 31.2 | 48.1 | 55.0 |
| Temperature, °C. | 278 | 278 | 278 | 340 | 338 | 338 |
| $C_3H_6$ Feed, WHSV | 0.4 | 0.4 | 0.4 | 0.4 | 0.4 | 0.4 |
| $C_3H_6$ Conversion, % | 10.99 | 7.14 | 6.51 | 22.76 | 11.81 | 9.81 |
| Product Selectivity, wt. % | | | | | | |
| $C_1$–$C_4$ | 44.7221 | 47.8693 | 55.9018 | 52.8577 | 56.1986 | 54.2018 |
| $C_5$–420° F. | 55.2779 | 47.8499 | 47.0982 | 41.8274 | 39.8977 | 41.7179 |
| 420° F.–700° F. | 0.0000 | 3.9954 | 0.0000 | 4.8751 | 3.6243 | 3.8083 |
| $C_5$–end point | 55.2779 | 52.1307 | 47.0982 | 47.1423 | 43.8014 | 45.7982 |
| Iso/normal mole ratio | | | | | | |
| $C_4$ | 5.8252 | — | 1.7902 | 2.2263 | 0.3878 | 0.3321 |
| $C_5$ | — | — | 10.6000 | 5.8028 | 0.0973 | 1.3918 |
| $C_6$ | 18.4058 | — | 7.3011 | 6.8580 | 1.8226 | 1.4639 |

In these two runs, catalyst deactivation occurred with time on stream, but the presence of steam due to the co-fed water stabilized the catalyst to some extent and assisted in slowing down the deactivation rate as compared with tests carried out using a ZSM-5 type catalyst at corresponding test levels, particularly at high temperature. The initial conversion level increased with temperature, as would be expected, but was much lower than that of said ZSM-5 type catalyst at corresponding temperatures. Maximum propylene conversions of about 11%, 23% and 50% were achieved, together with $C_5$ selectivities of about 55%, 47% and 44%, for the respective temperatures of 278° C., 338° C. and 408° C.

EXAMPLE II

An additional olefin run was carried out, as in Example I, but with an aluminum-extracted UHP-Y molecular sieve zeolite in place of the UHP-Y, not aluminum-extracted, that was used in said Example I. The aluminum extraction treatment will be understood to provide a UHP-Y zeolite of even milder activity than pertains for the untreated zeolite. The results of the run of this Example are best compared with those of Run 2 of Example I, and tend to demonstrate the effect of the aluminum extraction treatment. Thus, there are only slight differences in the reaction conditions for these two runs. While said Run 2 had a 1:1:3 $H_2:C_3H_6:H_2O$ mole ratio feed, the run of this Example had a 1:1:2 mole ratio feed. The effect of this difference in water level is seen as minor.

TABLE III

Propylene Conversion (with hydrogen diluent and co-fed water)

| Sample No. | 1 | 2 | 3 | 4 | 5 |
|---|---|---|---|---|---|
| Hours on Stream | 6.8 | 23.0 | 30.6 | 48.9 | 54.7 |
| Temperature, °C. | 283 | 281 | 341 | 338 | 338 |
| $C_3H_6$ Feed, WHSV | 0.5 | 0.5 | 0.5 | 0.5 | 0.5 |
| $C_3H_6$ Conversion, % | 10.56 | 7.66 | 13.21 | 11.45 | 11.44 |
| Product Selectivity, wt. % | | | | | |
| $C_1$–$C_4$ | 26.09 | 26.94 | 27.13 | 32.17 | 32.17 |
| $C_5$–420° F. | 68.24 | 71.23 | 65.25 | 66.24 | 65.60 |
| 420° F.–700° F. | 4.08 | 1.83 | 7.18 | 1.49 | 2.08 |
| 700° F.–end point | 1.59 | 0.00 | 0.25 | 0.09 | 0.15 |
| $C_5$–end point | 73.91 | 73.06 | 72.69 | 67.83 | 67.83 |
| Iso/normal mole ratio | | | | | |
| $C_4$ | 0.4781 | 0.2797 | — | 0.1035 | — |
| $C_5$ | 7.5735 | — | — | 1.0928 | — |
| $C_6$ | 0.5747 | 7.6118 | — | 3.7230 | — |

The catalytic activity of the aluminum-extracted UHP-Y was low, at a level of conversion similar to that obtained with untreated UHP-Y. The deactivation rate for said aluminum-extracted UHP-Y, herein referred to for convenience as UHP-Y(e), may be slightly less than for UHP-Y but this is not certain. Product selectivity for the UHP-Y(e), however, was very different than for UHP-Y. While neither catalyst showed significant cracking to $C_1$ or $C_2$ materials, UHP-Y(e) produced even less of such materials than UHP-Y. The greatest difference in selectivity was in the $C_3$ and $C_4$ saturates formation. Selectivity to butane was up slightly for UHP-Y(e), but propane production was down drastically. The selectivity to combined $C_3$ and $C_4$ saturates was less than half of that for said UHP-Y. These saturates, propane in particular, are formed by hydride transfer to the corresponding olefin. Such hydride transfer activity was found to be much lower in UHP-Y(e) than it had been in UHP-Y. This lowering of the propane production was the major reason for the increase in $C_5^+$ yield using UHP-Y(e), said yield being increased 35% at 280° C. and 50% at 340° C. relative to said UHP-Y.

EXAMPLE III

Comparative runs were also carried out with propylene feed using a conventional LZ-105-6 intermediate pore zeolite and the larger pore UHP-Y zeolite. The feed consisted of a mixture of propylene and hydrogen. The pressure was maintained at about 150 psig, with the conversion temperature being maintained at about 410° C. For most of the runs, the propylene was fed at 1 WHSV, with propylene and hydrogen being added at a 1:1 mole ratio thereof. Typical results using LZ-105-6 are shown in Table IV, while those using UHP-Y are shown in Table V.

TABLE IV

Propylene Conversion (with hydrogen diluent and LZ-105-6 Catalyst)

| Sample No. | 1 | 2 | 3 | 4 |
|---|---|---|---|---|
| Hours on Stream | 6.5 | 30.5 | 73.8 | 97.5 |
| Temperature, °C. | 410 | 410 | 409 | 408 |
| $C_3H_6$ Feed, WHSV | 1.0 | 1.0 | 1.0 | 1.0 |
| $C_3H_6$ Conversion, % | 97.23 | 86.69 | 33.19 | 10.70 |
| Product Selectivity, Wt. % | | | | |
| $C_1$–$C_4$ | 66.81 | 36.10 | 25.23 | 41.67 |
| $C_5$–420° F. | 26.37 | 59.59 | 73.92 | 58.28 |
| 420° F.–700° F. | 6.83 | 4.31 | 0.85 | 0.034 |
| $C_5$–end point | 33.19 | 63.90 | 74.77 | 58.33 |
| Iso/normal mole ratio | | | | |
| $C_4$ | 1.1081 | 1.6006 | 0.7019 | 0.5810 |
| $C_5$ | 3.0558 | 2.3316 | 0.8286 | 0.4384 |
| $C_6$ | 6.5961 | 2.6188 | 0.8418 | 0.7298 |
| FIA, wt. % | | | | |
| Aromatics | 94.3 | 48.2 | 6.2 | 25.0 |
| Olefins | 1.9 | 43.2 | 93.8 | 75.0 |
| Saturates | 3.8 | 8.6 | 0.0 | 0.0 |

TABLE V

Propylene Conversion (with hydrogen diluent and UHP-Y Catalyst)

| Sample No. | 1 | 2 |
|---|---|---|
| Hours on Stream | 3.75 | 8.0 |
| Temperature, °C. | 408 | 408 |
| $C_3H_6$ Feed, WHSV | 1.0 | 1.0 |
| $C_3H_6$ Conversion, % | 30.98 | 15.27 |
| Product Selectivity, wt % | | |
| $C_1$–$C_4$ | 53.99 | 43.20 |
| $C_5$–420° F. | 41.37 | 56.02 |
| 420° F.–700° F. | 4.57 | 0.71 |
| $C_5$–end point | 46.01 | 56.80 |
| Iso/normal mole ratio | | |
| $C_4$ | 1.1043 | 0.8488 |
| $C_5$ | 1.2801 | 0.7114 |
| $C_6$ | 1.6005 | 1.3779 |
| FIA, wt. % | | |
| Aromatics | 75.3 | 96.6 |
| Olefins | 19.7 | 3.4 |
| Saturates | 5.0 | 0.0 |

In the runs using LZ-105-6, conversion decreased with time, slipping below 50% at some time after 50 hours from an initial conversion level of nearly 100%. Even before such slippage, however, a dramatic and clear-cut pattern of decreasing conversion to aromatics, and of increasing production of olefins, was established. In the early stage of operations when the catalyst is active, the high aromatic-make was accompanied by high propane and butane make. This appears to confirm one of the characteristic phenomena of catalysis with strong acid zeolites, namely the facility to promote hydrogen redistribution among the hydrocarbons:

Olefins→Aromatics + Paraffins

When the catalyst deactivates, and presumably the strong sites are eliminated by coking, this is also the first activity to diminish. Skeletal isomerization activity as shown by the iso/normal ratio in the product underwent some reduction as well.

The larger pore zeolite of UHP-Y was observed to deactivate faster than the LZ-105-6. Experience has shown that runs using UHP-Y generally last from about 7 to about 14 hours on stream. Initial conversion using UHP-Y under the operating conditions of Table V was about 31%, but the catalyst demonstrated early deactivation characteristics as shown by the conversion of about 15% after 8 hours on stream. As compared with earlier UHP-Y runs at 277° C. and 340° C., the use of UHP-Y catalyst at said 400° C. of Table V resulted in an increase in product selectivity for $C_1$–$C_4$ light hydrocarbons and a decrease in $C_5$+ higher boiling hydrocarbons. In addition, the aromatics content of the product was also found to increase as the temperature increased.

It may appear, from the simple breakdown of products from LZ-105-6 and UPH-Y, that the LZ-105-6 is making as much diesel as the UPH-Y. The product from LZ-105-6 boiling above 400° F. is, however, just a slight tail, barely extending into the diesel range. The UHP-Y, on the other hand, produces hydrocarbon that boils throughout the diesel range. For a comparison of the relative boiling range of the condensed product hydrocarbon molecules made from the intermediate pore size LZ-105-6, and the large pore size UHP-Y of the invention, a portion of the $C_5$+ hydrocarbon liquid product was used to obtain simulated distillation data. The relative amounts of the condensed hydrocarbons collected, which varied according to the activity or the catalyst as reflected by its conversion level, were as tabulated in Table VI below.

TABLE VI

Relative Amount of Condensed Hydrocarbons

| Catalyst | LZ-105-6 | | | UHP-Y | |
|---|---|---|---|---|---|
| Table and Sample No. | IV - 1 | IV - 2 | IV - 3 | V - 1 | V - 2 |
| $C_3H_6$ Conversion, % | 97.2 | 72.8 | 33.2 | 31.0 | 15.3 |
| Product Selectivity | | | | | |
| $C_5$+, wt. % | 33.19 | 71.99 | 74.77 | 46.01 | 56.80 |
| Liq. Collected | 20.0 | 41.2 | 18.9 | 14.1 | 2.89 |
| Ratio Liq./$C_5$+ | 0.60 | 0.57 | 0.25 | 0.306 | 0.051 |

It should be noted that the LZ-105-6 sample 1 is product made using fresh LZ-105-6, exhibiting a high activity with a 97.2% conversion and the production of a large amount of aromatics. The results of samples 2 and 3 using LZ-105-6 are similar in nature, and the products are olefinic in nature. Of the two UHP-Y samples, the second is heavier in boiling range, but is not deemed representative of the $C_5$+ fraction as the amount of condensate recovered was so small that it constituted only a very small fraction, i.e. 5%, of the $C_5^{30}$ fraction, i.e. 95% of said $C_5$+ remained in the gas phase. A reasonable comparison, however, can be made between LZ-105, sample IV-3, and UHP-Y, sample V-1, because these two product samples were obtained at similar conversion levels, i.e. 33% and 31% respectively, and represent similar proportions of the respective total $C_5$+ fraction, i.e. 0.25 and 0.306 respectively. Simulated distillation data obtained at standard conditions are set forth in Table VII below.

TABLE VII

| | CATALYST | | |
|---|---|---|---|
| Sample No. | LZ-105-6 IV-3 | UHP-Y V-1 | DIFF. (UHP-Y-LZ-105-6) |
| Simulated Distillation | @ Deg. F | @ Deg. F | Deg. F |
| 10 wt. % @ Deg. F. | 165 | 249 | +84 |
| 16 | 203 | 279 | +76 |
| 50 | 286 | 383 | +97 |
| 84 | 357 | 505 | +148 |
| 90 | 384 | 560 | +176 |
| Range (16–84%) | 154 | 226 | +72 |

It will be seen that, at all levels of boiling point distribution, the liquid product collected from the UHP-Y Catalyst boils higher than that of LZ-105-6, on the average boiling about 116° F. higher. In addition, it should be noted that the boiling range is also wider, i.e. 72° F. wider for UHP-Y than for LZ-105-6. Such results demonstrate the potential advantage of UHP-Y catalyst for desirable use in the production of higher boiling liquid products.

By employing the steam-stabilized, zeolite Y catalyst of hydrophobic character as described and claimed herein, including the aluminum extracted form thereof, it has thus been found possible to advantageously convert light olefins to hydrocarbons useful for liquid motor fuels. Such desirable products boiling in the gasoline plus jet fuel and diesel oil boiling range, with only minor production of heavier products, are of value in meeting the needs of industrialized societies, such that the invention represents a desirable advance in the art of motor fuel production.

We claim:

1. A process for the conversion of linear and/or branched chain $C_2$ to $C_{12}$ olefins to hydrocarbon mixtures having enhanced suitability for use as liquid motor fuels comprising contacting said olefins, without the necessity of recycle of product, with a catalyst comprising a steam-stabilized, hydrophobic zeolite Y catalyst, under conditions effective to produce the resulting hydrocarbon product comprising up to about $C_{22}$ material boiling in the gasoline and jet fuel+diesel oil boiling range and having relatively minor amounts of heavy products boiling beyond the diesel oil range.

2. The process of claim 1 in which said zeolite Y catalyst has an $SiO_2/Al_2O_3$ molar ratio equal to or greater than 4.5, the essential x-ray powder diffraction pattern of zeolite Y, a unit cell dimension, $a_o$, of less than 24.45 Angstroms, a sorptive capacity of water vapor at 25° C. and a $p/p_o$ value of 0.10 of less than 10.0 weight percent.

3. The process of claim 2 in which said water adsorption capacity is less than about 4.0 weight percent.

4. The process of claim 2 in which said olefins comprise $C_3$ to $C_4$ olefins.

5. The process of claim 1 in which said catalytic conversion reaction is carried out at a temperature of from about 100° C. to about 450° C.

6. The process of claim 5 in which said reaction temperature is from about 240° C. to about 420° C.

7. The process of claim 1 in which said catalytic conversion reaction is carried out at a pressure of from about 0 to about 1,000 psig.

8. The process of claim 7 in which said reaction pressure is from about 0 to about 350 psg.

9. The process of claim 1 in which said catalyst comprises said zeolite Y in aluminum-extracted form.

10. The process of claim 9 in which the alumina content of said aluminum-extracted zeolite is less than about 3 weight %.

11. The process of claim 9 in which said olefins comprise $C_3$ to $C_4$ olefins.

12. The process of claim 4 in which said olefins comprise propylene.

13. The process of claim 9 in which said olefins comprise propylene.

14. The process of claim 1 wherein said olefins are contacted with the catalyst in the presence of a diluent selected from the group consisting of $C_1$–$C_{14}$ paraffins, nitrogen, carbon dioxide, hydrogen, water and mixtures thereof.

15. The process of claim 14 in which said diluent comprises water.

16. The process of claim 15 in which the mole ratio of water to olefin is in the range of from about 1 to about 95% by weight.

17. The process of claim 15 in which said olefins comprise $C_3$ to $C_4$ olefins.

18. The process of claim 17 in which said olefins comprise propylene.

19. The process of claim 18 in which said catalyst comprises said zeolite Y in aluminum-extracted form.

20. The process of claim 19 in which said water adsorption capacity is less than about 4.0 weight percent.

21. A process for the conversion of linear and branched chain $C_2$ to $C_{12}$ olefins, and mixtures thereof, to hydrocarbon mixtures suitable for use as liquid motor fuels which comprise up to about $C_{22}$ material, boiling in the gasoline and jet fuel+diesel oil boiling range and having relatively minor amounts of heavy products boiling beyond the diesel oil range, said process comprising the contacting of said olefins with a catalyst comprising a steam-stabilized, hydrophobic zeolite Y catalyst in aluminum-extracted form under conditions effective to produce such hydrocarbon mixtures.

22. The process of claim 21 in which the hydrocarbon mixture product is not recycled to increase the proportion of the product boiling in the jet fuel+diesel oil range.

23. The process of claim 21 in which said olefins are contacted with said catalyst in admixture with a diluent selected from the group consisting of $C_1$ to $C_{14}$ paraffins, nitrogen, carbon dioxide, hydrogen, water and mixtures thereof.

* * * * *